US007699817B2

(12) United States Patent
Adams

(10) Patent No.: US 7,699,817 B2
(45) Date of Patent: Apr. 20, 2010

(54) DEVICE FOR MONITORING THE ADMINISTRATION OF ENTERAL NUTRITIONAL FLUIDS INTO A FEEDING TUBE

(75) Inventor: Mark L. Adams, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1659 days.

(21) Appl. No.: 10/808,813

(22) Filed: Mar. 25, 2004

(65) Prior Publication Data

US 2005/0215948 A1 Sep. 29, 2005

(51) Int. Cl.
*A61M 37/00* (2006.01)

(52) U.S. Cl. ........................ 604/246; 604/256; 604/910

(58) Field of Classification Search ................. 604/131, 604/67, 151, 65, 246, 255, 256, 910, 890.1
See application file for complete search history.

(56) References Cited

U.S. PATENT DOCUMENTS

| | | | | |
|---|---|---|---|---|
| 4,688,595 | A | 8/1987 | Srebnik et al. | |
| 5,562,615 | A | 10/1996 | Nassif | |
| 5,951,510 | A * | 9/1999 | Barak | 604/67 |
| 6,416,496 | B1 * | 7/2002 | Rogers et al. | 604/132 |
| 2005/0256447 | A1 * | 11/2005 | Richardson et al. | 604/65 |

* cited by examiner

*Primary Examiner*—Nicholas D Lucchesi
*Assistant Examiner*—Laura A Bouchelle
(74) *Attorney, Agent, or Firm*—Kenyon & Kenyon LLP

(57) ABSTRACT

A monitoring device is coupled to the open proximal end of an implanted gastrostomy feeding tube in order to monitor the administration of enteral nutritional fluids into the body of the patient. The monitoring device includes a clamshell-like casing and an electronic control circuit mounted within the casing. The casing includes upper and lower housings which are coupled together about a hinge. The casing additionally includes a connector shaped to fittingly project into the open proximal end of the feeding tube, the connector defining a lumen in fluid communication with the longitudinally-extending bore of the tube. A metering device is disposed within the lumen in the casing and is electrically connected to the control circuit. In use, the monitoring device is capable of, among other things, measuring the duration of a particular feeding period, measuring the duration between subsequent feeding periods, and measuring the delivery rate and amount of fluid that passes through the lumen during a feeding period, the results of the measurements being provided on an externally-viewable display.

41 Claims, 4 Drawing Sheets

DEVICE FOR MONITORING THE ADMINISTRATION OF ENTERAL NUTRITIONAL FLUIDS INTO A FEEDING TUBE

BACKGROUND OF THE INVENTION

The present invention relates generally to monitoring the administration of enteral nutritional fluids to a feeding tube which has been implanted in the body of a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method").

After a PEG device is implanted, the proximal portion of the implanted gastrostomy feeding tube is typically severed to reduce the externally-extending portion of the tube to a desired length (typically about 4-6 inches). An external bolster is then secured to the remaining exposed length of the implanted tube to prevent the retraction of the tube into the patient's stomach.

A "Y-port" adaptor is commonly attached to the proximal end of the implanted feeding tube. The Y-port adaptor is typically constructed as a unitary, tubular member made of silicone or the like which includes an unbranched distal end and a branched proximal end. The unbranched distal end of the Y-port adaptor is typically connected to the proximal end of the implanted feeding tube using a tubular connector. The branched proximal end of the Y-port adaptor is typically shaped to include a pair of lumens, a larger diameter lumen and a smaller diameter lumen. The larger diameter lumen is adapted to receive the dispensing tip of a syringe or feeding set adapter of the type through which food is typically dispensed. The smaller diameter lumen is adapted to receive the dispensing tip of a syringe or feeding set adapter of the type through which medication is typically dispensed.

The Y-port adaptor also typically includes a pair of tethered plugs, the plugs being used to 'cap' the lumens when the lumens are not in use (the Y-port adaptor typically remaining secured at all times to the proximal end of the feeding tube). In this manner, the plugs prevent undesired materials from entering the patient through the Y-port adaptor. At the same time, the plugs are also intended to prevent the escape of the patient's stomach contents through the Y-port adaptor.

Enteral nutritional fluids are typically administered to a patient using either a bolus feeding technique or a drip feeding technique.

In the bolus feeding technique, enteral nutritional fluids are manually administered to the patient using a conventional syringe. Specifically, the dispensing tip of a syringe which contains the required nutritional fluids is inserted into the larger diameter lumen of the Y-port. The nutritional fluid is then administered to the patient by applying a manual dispensing force to the plunger of the syringe.

Although effective in administering nutritional fluids to a patient, the bolus feeding technique suffers from a few notable drawbacks.

As a first drawback, the bolus feeding technique provides the fluid administering party with limited control of the rate in which the fluid is dispensed into the patient. In fact, the rate of fluid administration is directly dependent upon the injection force applied to the syringe plunger by the fluid administering party. As a consequence, it has been found that nutritional fluids administered using the bolus feeding technique are often delivered to a patient at an unacceptably fast rate. The administration of enteral nutritional fluids at such a fast rate can undesirably cause the patient to experience, inter alia, abdominal pain, gas, and/or bloating.

As a second drawback, the bolus feeding technique requires continuous human intervention, thereby rendering the bolus technique considerably labor intensive. Specifically, the person responsible for the administration of the fluid (e.g., a nurse, a trained professional, or even the patient himself) is required to manually dispense all of the syringe contents by depressing the syringe plunger. This can be time-consuming as the bolus administration of 200 cc of nutritional fluids can often take as long as 30 minutes.

Due to the aforementioned drawbacks associated with the bolus feeding technique, it has been found that drip feeding techniques for administering enteral nutritional fluids into the body of a patient are typically preferred.

In the drip feeding technique, enteral nutritional fluids are typically packaged within a deformable supply pouch. A fluid delivery set, also referred to herein as a feeding set, serves a conduit through which the fluids can travel from the supply pouch and into a desired lumen of the Y-port. The fluid delivery set commonly includes a drip chamber having an inlet which is adapted to receive, directly or through a connecting piece of flexible tubing, nutritional fluids from the supply pouch. The outlet of the drip chamber is connected to an elastically flexible tubing, such as a silicone rubber tube, or interconnected lengths thereof, which is in turn inserted into the desired lumen of the Y-port via an adaptor.

The fluid which collects within the feeding set drip chamber is typically transported to the Y-port either through the use of natural gravitational forces (i.e., disposing the supply pouch at a height above the Y-port) or through the use of an enteral feeding pump.

A rotary peristaltic pump is one well known type of enteral feeding pump. A rotary peristaltic pump commonly includes a motor driven peristaltic rotor mounted on a shaft which extends out through the front wall of the pump housing. The peristaltic rotor carries an array of equidistantly spaced rollers along its outer periphery. The elastically flexible tubing which connects the outlet of the drip chamber to the Y-port is wrapped around the rotor in tension against the plurality of rollers. Accordingly, as the rotor is rotated, the rollers squeeze the flexible tubing so as to force a predetermined amount of the fluid through the flexible tubing by means of the squeezing action. The pump is typically provided with an electronic control circuit for regulating the operation of the rotor which, in turn, controls the rate and schedule of fluid administration into the body of the patient. Based on the operation of the rotor, the control circuit can calculate the amount of fluid dispensed to the Y-port (and, in turn, to the patient) over one or more feeding periods.

The use of an enteral feeding pump to transport enteral nutritional fluids from the feeding set drip chamber to the implanted feeding tube provides a number of significant advantages over the use of natural gravitational forces to transport enteral nutritional fluids from the feeding set drip chamber to the implanted feeding tube.

As a first advantage, the utilization of an enteral feeding pump allows for the metering of a specified amount of nutritional fluid to the patient. In this capacity, an enteral feeding pump can ensure that a patient ultimately receives the proper amount of nutritional fluid, which is highly desirable. In fact, once the pump determines that the proper amount of fluid has been delivered to the patient, the feeding pump will terminate further rotation of the rotor. In addition, if the proper amount of fluid is not delivered to the patient over a specified period of time, the pump can be programmed to activate an alarm which is electrically connected to the pump control circuit. To the contrary, gravitational feeding techniques are only capable of delivering a non-adjustable amount of fluid to the patient (i.e., the amount of fluid contained within the supply pouch).

As a second advantage, the utilization of an enteral feeding pump allows for the rate of fluid administration to be adjusted (typically between 5 ml/hr to 75 ml/hr) as deemed necessary to maximize the effectiveness in which the patient absorbs the nutrients in the fluid. To the contrary, gravitational feeding techniques are more limited in their maximum fluid feed rates as they are dependent upon the fluid level within the pouch and the height of the pouch relative to the implanted feeding tube.

As a third advantage, the utilization of an enteral feeding pump allows for intermittent feeding at user-specified feeding cycles. Specifically, the control circuit of the feeding pump can be programmed to monitor the time which has elapsed since the last feeding period and, in turn, re-commence the feeding process once the elapsed time reaches a pre-defined level. To the contrary, gravitational feeding techniques only allow for a single, uninterrupted feeding period.

Although well-known and widely used in the art, one problem is commonly associated with the use of enteral feeding pumps. Specifically, enteral feeding pumps of the type described above are commonly shared amongst a plurality of patients. For example, in certain situations (e.g., a hospital or nursing home), a single pump can be used to routinely administer enteral nutritional fluids for a large group of patients who have distinct feeding requirements. Because a single pump is often used to dispense fluids for multiple patients, it is essential that the pump be constantly re-programmed to match the precise fluid administration requirements of a particular patient. If the feeding pump is not properly re-programmed in accordance to the precise fluid administration requirements of a particular patient, said patient becomes susceptible to improper feedings, which is highly undesirable.

SUMMARY OF THE INVENTION

It is an object of the present invention to provide a device for monitoring the administration of enteral nutritional fluids into a feeding tube, such as a gastrostomy feeding tube, which has been implanted in the body of a patient.

It is another object of the present invention to provide a monitoring device as described above that monitors and displays the rate in which the fluid is administered to the patient.

It is yet another object of the present invention to provide a monitoring device as described above that monitors and displays the quantity of fluid which is administered to the patient.

It is still another object of the present invention to provide a monitoring device as described above that monitors and displays the schedule in which the fluid is administered to the patient.

It is yet still another object of the present invention to provide a monitoring device that is permanently coupled to the feeding tube for the patient.

It is another object of the present invention to provide a monitoring device that has a limited number of parts, is inexpensive to manufacture and is easy to use.

Therefore, there is provided the combination of a feeding tube and a device for monitoring the administration of enteral nutritional fluids into the feeding tube, said feeding tube including a longitudinally-extending bore and an open proximal end, said monitoring device comprising a casing coupled to the open proximal end of said feeding tube, said casing being shaped to define a lumen in fluid communication with the longitudinally-extending bore of said feeding tube, said lumen including an inlet and an outlet, and an electronic control circuit mounted within said casing.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate an embodiment of the invention and, together with the description, serve to explain the principles of the invention. In the drawings wherein like reference numerals represent like parts.

DETAILED DESCRIPTION OF PREFERRED EMBODIMENTS

Figure 1:
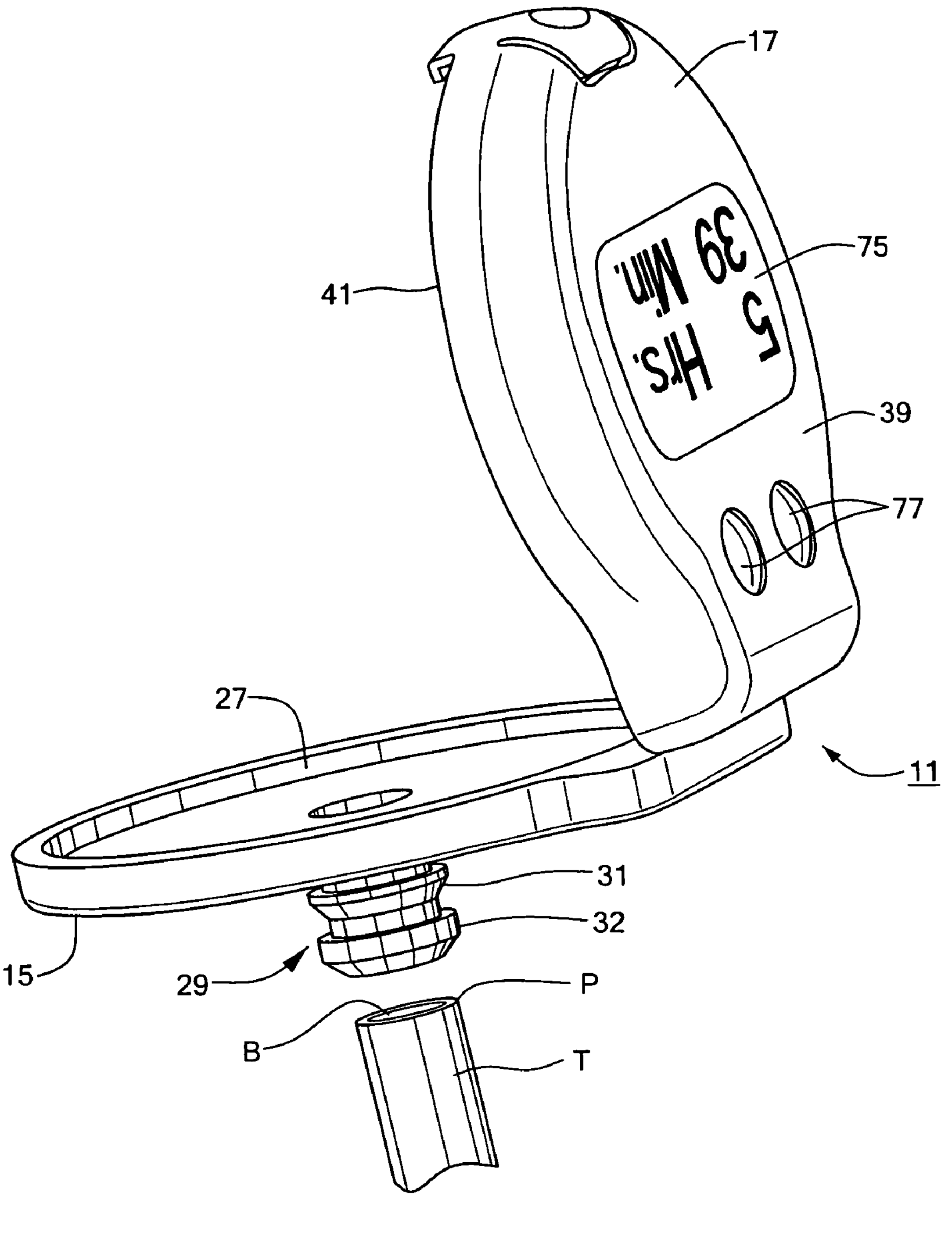
FIG. 1 is a right side perspective view of a monitoring device constructed according to the teachings of the present invention, the monitoring device being shown spaced apart from a fragmentary length of a gastrostomy feeding tube, the monitoring device being shown with its upper housing disposed in its open position.

Referring now to FIGS. 1-4, there are shown right side perspective, top perspective, front perspective and simplified electrical schematic views, respectively, of a device for monitoring the administration of enteral nutritional fluids into the body of a patient, said monitoring device being constructed according to the teachings of the present invention and represented generally by reference numeral 11. As will be described further in detail below, protective device 11 is adapted to be permanently coupled to the open proximal end P of an implanted gastrostomy feeding tube T, either directly or through one or more connective pieces of tubing (e.g., a Y-port). (It should be noted that, although device 11 is shown and described herein as being coupled to a gastrostomy feeding tube, device 11 may alternatively be coupled to a jejunostomy feeding tube or to other types of feeding tubes.)

Figure 2:
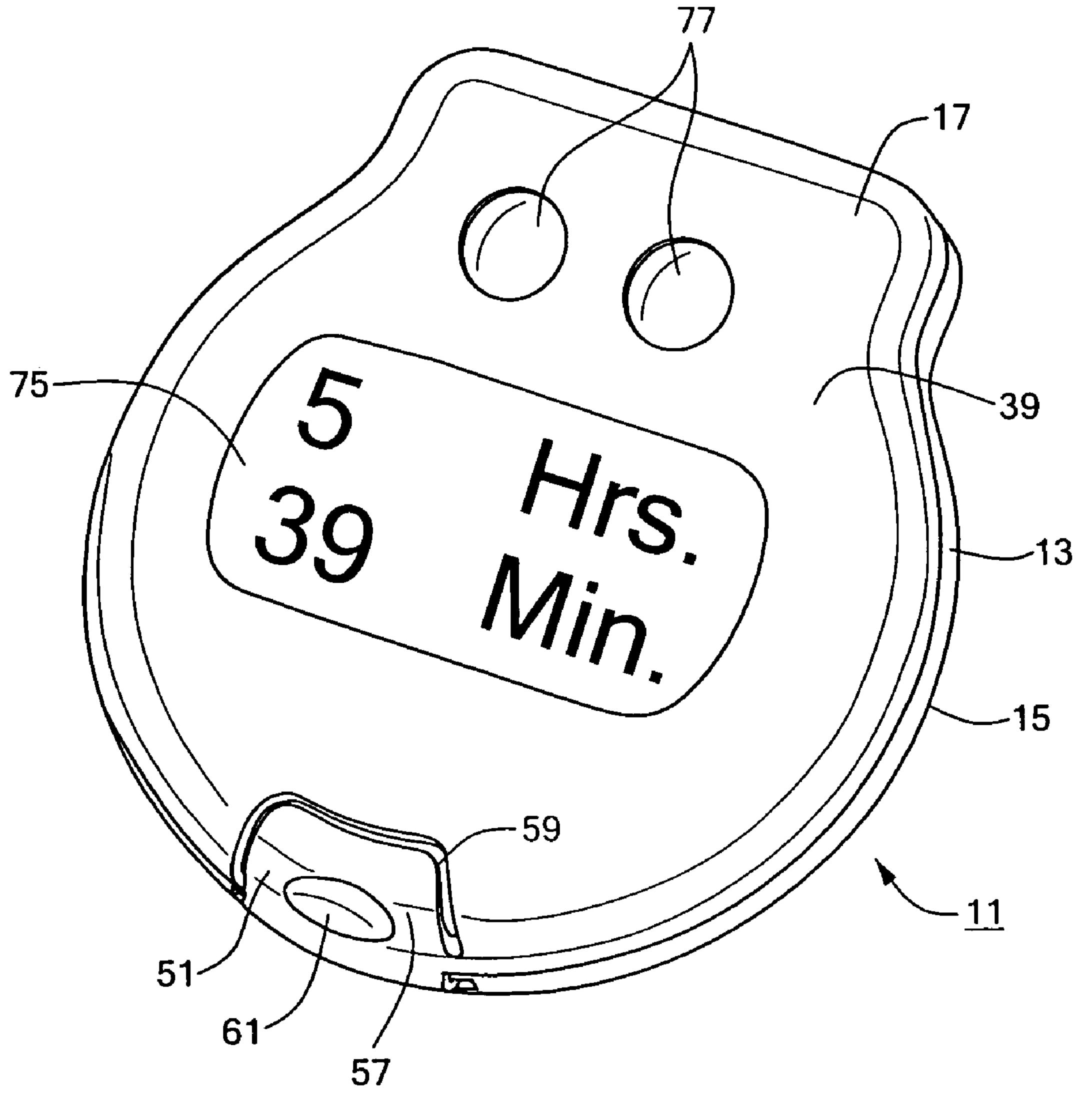
FIG. 2 is a top perspective view of the monitoring device of FIG. 1, the monitoring device being shown with its upper housing disposed in its closed position.

Protective device 11 comprises a casing 13 which is constructed of a rigid and durable material such as plastic. Casing 13 has a clamshell-like construction and includes a lower housing 15 and an upper housing 17 which are pivotally connected about a hinge 19. In this manner, upper housing 17 can be pivotally disposed relative to lower housing 15 between an open position (as shown in FIG. 1) and a closed position (as shown in FIG. 2).

Figure 3:
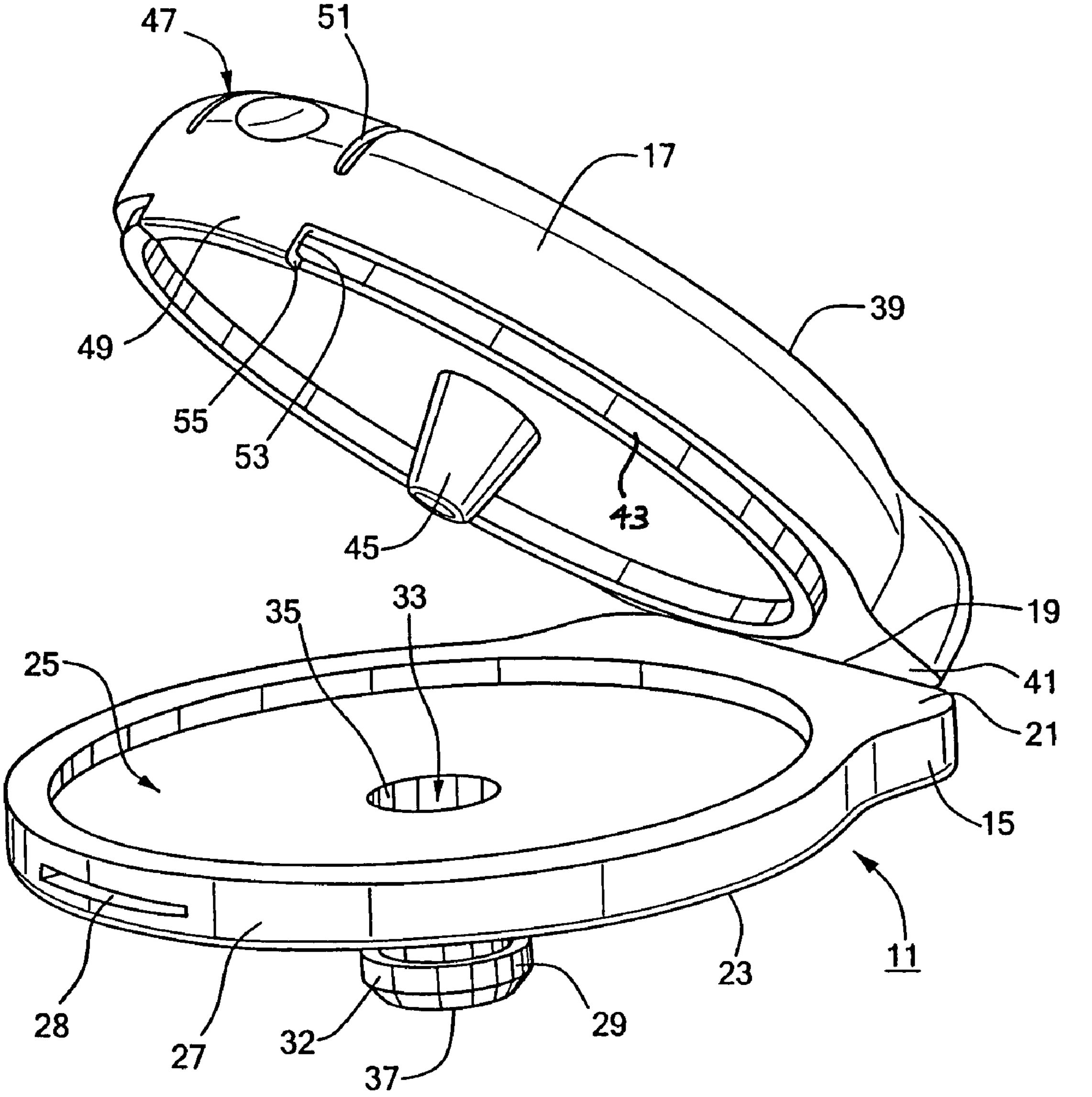
FIG. 3 is a front perspective view of the monitoring device of FIG. 1, the monitoring device being shown with its upper housing disposed at a location between its open and closed positions.
Figure 4:
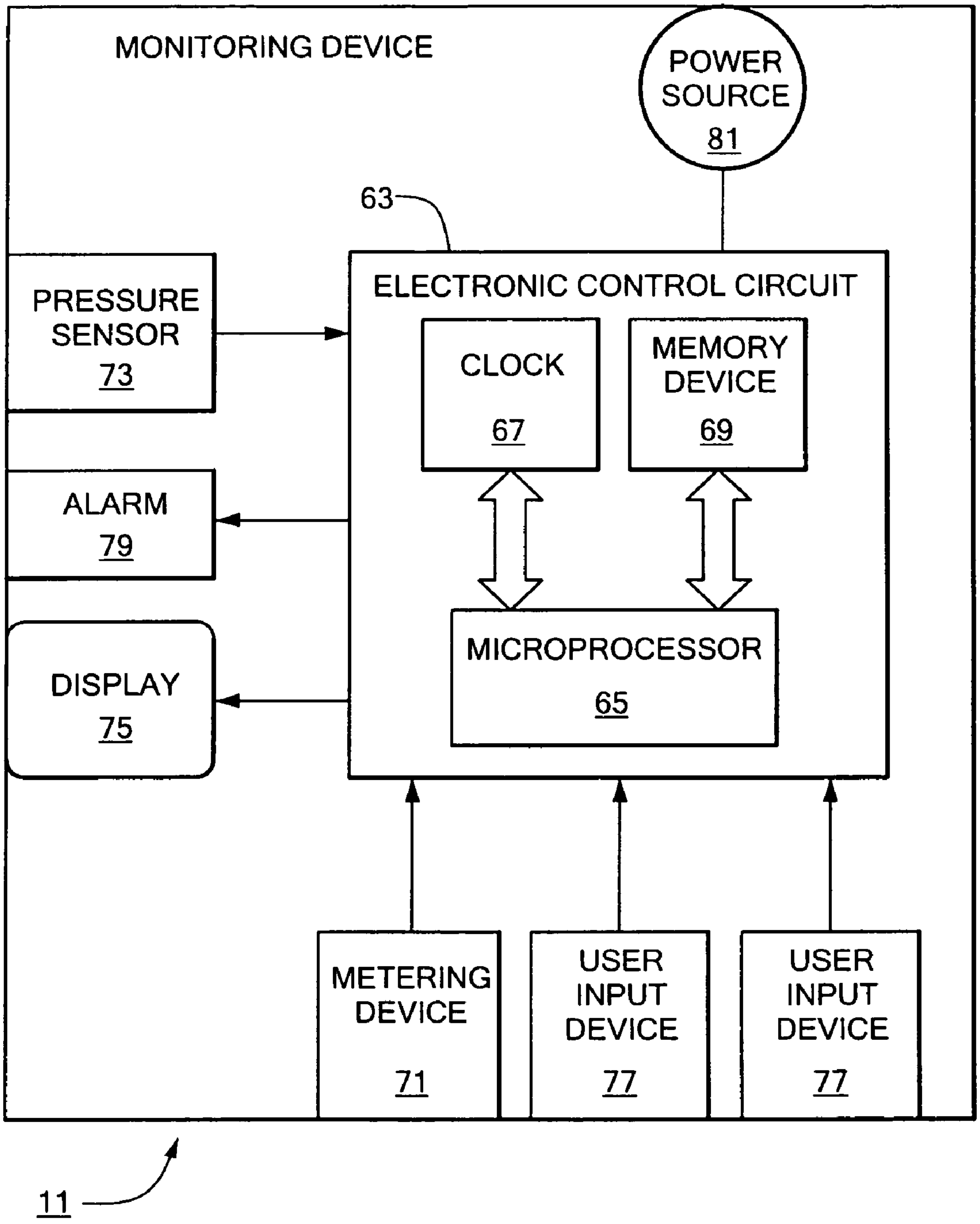
FIG. 4 is a simplified electrical schematic representation of the monitoring device of FIG. 1.

As seen most clearly in FIG. 3, lower housing 15 is preferably in the form of an integral piece which can be manufactured using conventional injection molding techniques. Lower housing 15 is generally annular in lateral cross-section and includes a substantially flat top surface 21 and a substantially flat bottom surface 23. A shallow circular recess 25 is formed in the majority of top surface 21 which, in turn, serves to create a thin flange, or wall, 27 that defines the outer periphery of recess 25. The front end of flange 27 is shaped to define a thin lateral slot 28 which can be used to lockably retain upper housing 17 in its closed position, as will be described further in detail below.

A cylindrical tube connector 29 projects orthogonally out from bottom surface 23. As shown most clearly in FIG. 1, connector 29 is sized and shaped to be inserted into an open end of a length of silicone tubing (e.g., into the open proximal end P of implanted gastrostomy feeding tube T or into the larger diameter lumen of a Y-port). Preferably, connector 29 is shaped to include first and second outwardly projecting barbs 31 and 32 which are spaced apart along its length. Barbs 31 and 32 are sized and shaped to engage the interior surface of the silicone tubing into which connector 29 is inserted. In this manner, barbs 31 and 32 serve to fixedly secure tube connector 29 of protective device 11 within the length of silicone tubing T.

Connector 29 defines a lumen 33 which is generally circular in lateral cross-section. Lumen 33 extends transversely through lower housing 15 and includes an inlet 35 and an outlet 37. As will be described further in detail below, inlet 35 is sized and shaped to receive an adaptor for a feeding set.

Upper housing 17 is preferably an integral member which can be manufactured using conventional injection molding techniques. Upper housing 17 is generally disc-shaped in construction and includes a substantially flat top surface 39 and a substantially flat bottom surface 41.

A circular ring 43 protrudes out from flat bottom surface 41. With upper housing 17 pivoted into its closed position, circular ring 43 is configured to project into shallow recess 25 with the outer portion of circular ring 43 in frictional engagement against the inner surface of flange 27. In this manner, the frictional engagement between ring 43 and flange 27 serves to help retain upper housing 17 in its closed position in the absence of a considerable opening force.

A conical protrusion 45 protrudes orthogonally out from flat bottom surface 41. With upper housing 17 pivoted into its closed position, protrusion 45 is configured to fittingly project into lumen 33 in a seal-tight relationship. As a result, with upper housing 17 pivoted closed, undesired materials from the patient (e.g., stomach contents) are incapable of passing out through inlet 35 of lumen 33.

Upper housing 17 is provided with an articulating locking member 47 for releasably securing upper housing 17 in its closed position. Locking member 47 includes an L-shaped latch 49 and an pivotable actuation member 51.

L-shaped latch 49 includes an arm 53 which extends orthogonally out from bottom surface 41 of upper housing 17 at its front end. A shoulder 55 is formed onto the free end of arm 53 and extends orthogonally inward. Shoulder 55 is sized and shaped to protrude into slot 28 in lower housing 15 when upper housing 17 is disposed in its closed position. In this manner, shoulder 55 serves to releasably secure upper housing 17 in its closed position.

As seen most clearly in FIG. 2, actuation member 51 includes a rectangular tab 57 which is bounded on three sides by a U-shaped score line 59. Preferably, tab 57 is provided with a circular depression 61 which is ergonomically shaped to receive a finger. Score line 59 enables tab 57 pivot upon the application of a downward force on depression 61. Specifically, with shoulder 55 protruding into slot 28 so as to lock upper housing 17 in its closed position, the application of a downward force on depression 61 causes the inner end (i.e., the unsecured end) of tab 57 to pivot downward which, in turn, causes shoulder 55 of L-shaped latch 49 to pivot outward. As latch 49 pivots outward, shoulder 55 withdraws from slot 28, thereby releasing upper housing 17 from lower housing 15. With upper housing 17 released from lower housing 15, upper housing 17 can be pivoted to its open position.

Preferably, upper housing 17 is shaped to include an enclosed interior cavity which is sized and shaped to receive an electronic control circuit 63 responsible for the management of all the electronic operations of monitoring device 11. As seen most clearly in FIG. 4, electronic control circuit 63 includes a microprocessor 65, a clock 67 and a memory device 69 which are all preferably electrically connected through a common printed circuit board (not shown).

Microprocessor 65 is an application specific integrated circuit (ASIC) that functions as the central processing unit for monitoring device 11. As a result, microprocessor 65 is responsible for the principal operations (e.g., calculations and data management tasks) required by monitoring device 11 during use.

Clock 67 is electrically connected to microprocessor 65 and provides monitoring device 11 with time monitoring capabilities. Specifically, the types of information that may be acquired using clock 67 include determining the elapsed time between subsequent feeding periods and the elapsed time of a particular feeding period.

Memory 69 is electrically connected to microprocessor 65 and provides monitoring device 11 with the ability to retain data processed by microprocessor 65, said data being available for subsequent retrieval. As a result, various types of information relating to the feeding history of a patient can be stored in memory 69. Examples of the type of information which may be stored in memory 69 include, inter alia, the duration of one or more feeding periods, the particular time when the one or more feeding periods started and/or stopped, the feeding rate of the one or more feeding periods and the amount of fluid administered during the one or more feeding periods.

A metering device 71 is electrically connected to control circuit 63 and provides monitoring device 11 with the ability to monitor the amount of fluid which is ultimately delivered to the patient. Metering device 71 is preferably in the form of a metal or plastic disc which is fixedly secured to lower housing 15 within lumen 33. Metering device 71 preferably includes a pressure sensitive material which defines a circular opening approximately 0.25 inches in diameter, said pressure sensitive material being electrically connected to control circuit 63. Metering device 71 is disposed within lumen 33 such that fluids which pass through lumen 33 are, in turn, detected by the pressure sensitive material of metering device 71. In this capacity, metering device 71 is able to transmit an electrical signal to control circuit 63 in response to the detection of fluid passing therethrough, the electrical signal, in turn, being processed by control circuit 63 to determine the amount of fluid which is dispensed through monitoring device 11 and ultimately into the patient during a feeding period, which is highly desirable.

A pressure sensor 73 is electrically connected to control circuit 63 and provides monitoring device 11 with the ability to determine whether upper housing 17 is disposed in its closed position. In this capacity, pressure sensor 73 can provide an electrical signal to control circuit 63 which signifies that a particular feeding period is beginning (i.e., when upper housing 17 is pivoted open) or ending (i.e., when upper housing 17 is pivoted closed). Pressure sensor 73 is preferably in the form of a strip of pressure sensitive material which is fixedly secured to a portion of casing 13 at a location that would result in sensor 73 being contacted only when upper housing 17 is disposed in its closed position. Examples of potential mounting sites for pressure sensor 73 include, inter alia, on top surface 21 of lower housing 15, on bottom surface 41 of upper housing 17, or on the free end of ring 43.

A display 75 is electrically connected to control circuit 63 and provides monitoring device 11 with the ability to visually display pertinent data accumulated by control circuit 63. Display 75 is represented herein as being in the form of a liquid crystal display (LCD) which is capable of displaying numerical and alphabetical characters. Preferably, display 75 is designed to provide a running digital counter which is capable of displaying a running elapsed time (e.g., of the type commonly found in a digital watch or digital stopwatch). Display 75 is mounted within upper housing 17 in such a manner so as align within a transparent window formed in top surface 39, thereby rendering display 75 is externally viewable.

A pair of user input devices 77 are mounted in upper housing 17, each device 77 being positioned to partially project through a corresponding opening formed in top surface 39. Each user input device 77 is represented herein as an externally accessible control button which can be used to manually control the primary operations of monitoring device 11. Specifically, the depression of each device 77 serves to close an associated open switch in control circuit 63 which, in turn, transmits an electrical signal to microprocessor 65. In this manner, user input devices 77 can be used, among other things, to start/stop a timer, to reset a timer, and/or to scroll through a menu of operations which can be performed by monitoring device 11.

An alarm 79 is electrically connected to control circuit 63. Alarm 79 represents any visual or audible indicator which can be activated by control circuit 63. In this capacity, control circuit 63 can activate alarm 79 if any deviation from a programmed feeding schedule (e.g., if the nutritional fluid to be administered to the patient runs out or if the elapsed time between feeding periods advances past a pre-determined threshold).

Control circuit 63 preferably derives power from a power source 81 disposed within upper housing 17 of casing 13. Power source 81 may be in the form of one or more replaceable AA-type batteries which are removably mounted into an associated battery compartment and which are accessible through a removable cover. However, it is to be understood that any source of power capable of providing a suitable direct (DC) voltage can be used to provide power to control circuit 63.

Monitoring device 11 can be used in the following manner to monitor the administration of enteral nutritional fluids into a gastrostomy feeding tube T which has been implanted into the body of a patient. With upper housing 17 lockably disposed in its closed position, monitoring device 1 is permanently coupled to open proximal end P of implanted gastrostomy feeding tube T. For simplicity purposes only, monitoring device 11 will be described as being mounted directly onto open proximal end P of implanted gastrostomy feeding tube T. However, it is to be understood that monitoring device 11 could, in the alternative, be secured to a connective piece of tubing (e.g., a Y-port) which is in turn directly or indirectly coupled to open proximal end P of implanted gastrostomy feeding tube T without departing from the spirit of the present invention.

Monitoring device 11 is coupled to implanted gastrostomy feeding tube T by inserting tube connector 29 into open proximal end P. With connector 29 properly inserted, barbs 31 and 32 engage the interior surface of feeding tube T to permanently secure monitoring device 11 thereto. It should be noted that, with connector 29 inserted into open proximal end P, the longitudinally-extending bore B defined by feeding tube T is in direct fluid communication with lumen 33 of monitoring device 11.

Having affixed monitoring device 11 to implanted feeding tube T in the manner described above, the party responsible for the administration of enteral nutritional fluids to the patient (said party being referred to herein simply as the administering party) may operate clock 67 using user input devices 77, the operation of clock 67 being visually provided on display 75. In this manner, the administering party is able to commence a running counter which signifies the elapsed time since the last feeding period. Potentially, control circuit 63 could be programmed such that once the running counter reaches a particular value, alarm 79 would be activated to signify that the next feeding period has been reached.

Once the administering party determines that a feeding period has been reached (i.e., that enteral nutritional fluids need to be delivered immediately to the patient), tab 57 of actuation member 51 is depressed which, in turn, unlocks upper housing 17 from lower housing 15. With upper housing 17 unlocked from lower housing 15, upper housing 17 is pivoted to its open position. It should be noted that, once upper housing 17 is pivoted open, pressure sensor 73 transmits a signal to control circuit 63 which signifies that upper housing 17 has been pivoted open. The signal transmitted from pressure sensor 73 to control circuit 63 can then be used to automatically stop and reset the operation of the running counter which measures the elapsed time between feeding periods.

In order to administer fluids to the patient, an adaptor for the feeding set is fittingly disposed within inlet 35 of lumen 33. The fluids contained within the supply pouch of the feeding set are then transported into implanted feeding tube T via lumen 33 of monitoring device 11 using any conventional drip-feeding delivery technique (e.g., using a rotary peristaltic pump). As the fluid travels through lumen 33, metering device 71 detects the flow of said fluid and, in response thereto, transmits an electrical signal to control circuit 63. Either automatically or through the use of input devices 77, control circuit 63 may determine, among other things, the following types of data relating to the administration of said fluid to the patient: the rate of fluid delivery to the patient, the cumulative amount of fluid delivered to the patient (which can be manually or automatically reset after each feeding period) and/or the elapsed time of a particular feeding period. Preferably, the data is provided on display 75 to assist the administrating party in delivering the fluids to the patient in accordance with doctor-specified guidelines and, in addition, the data is stored in memory device 69 if historical analysis is required. Furthermore, control circuit 63 may be programmed to activate alarm 79 if any piece of accumulated data substantially deviates from the doctor-specified guidelines.

Once a feeding period has completed, the administrating party withdraws the adaptor for the feeding set from inlet 35 of lumen 33 and pivots upper housing 17 closed. As upper housing 17 is pivoted closed, latch 49 eventually projects into slot 28 to secure upper housing 17 in its closed position. With upper housing 17 pivoted closed, protrusion 45 forms a seal-tight fit within lumen 33. In this manner, protrusion 45 prevents undesired materials from entering the patient through implanted feeding tube T. At the same time, protrusion 45 also serves to prevent the escape of the patient's stomach contents out through inlet 35 of lumen 33.

In addition, the closure of upper housing 17 also causes pressure sensor 73 to be activated which, in turn, transmits a corresponding electrical signal to control circuit 63. In response thereto, control circuit 63 may automatically activate a running counter using clock 67. The running counter would preferably be shown on display 75 and would signify the elapsed time since the last feeding period. With the running counter activated, historical data relating to prior feeding periods could be retrieved by the administering party from memory device 69 using input devices 77. The above-described process for administering fluids to the patient can be repeated as deemed necessary.

The embodiment of the present invention described above is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. The combination of:

(a) an enteral feeding tube, said enteral feeding tube including a longitudinally-extending bore and an open proximal end, and (b) a device for monitoring the administration of enteral nutritional fluids into the open proximal end of said enteral feeding tube, said device comprising, (i) a casing coupled to the open proximal end of said enteral feeding tube, said casing being shaped to define a lumen in fluid communication with the longitudinally-extending bore of said enteral feeding tube, said lumen including an inlet and an outlet, (ii) an electronic control circuit mounted within said casing, and (iii) a metering device positioned within the lumen to measure fluid flow therethrough.

2. The combination as claimed in claim 1 wherein said metering device is in electrical connection with said control circuit.

3. The combination of:

(a) a feeding tube, said feeding tube including a longitudinally-extending bore and an open proximal end, and (b) a device for monitoring the administration of enteral nutritional fluids into the open proximal end of said feeding tube, said device comprising, (i) a casing coupled to the open proximal end of said feeding tube, said casing being shaped to define a lumen in fluid communication with the longitudinally-extending bore of said feeding tube, said lumen including an inlet and an outlet, (ii) an electronic control circuit mounted within said casing, and (iii) a metering device in electrical connection with said control circuit, wherein said metering device is positioned within the lumen and coupled to said casing.

4. The combination as claimed in claim 3 wherein said metering device includes a pressure-sensitive material which generates an electrical signal in response to fluid passing through the lumen.

5. The combination as claimed in claim 4 wherein said control circuit, in response to receiving an electrical signal from said metering device, calculates the amount of fluid which passes through the lumen.

6. The combination as claimed in claim 4 wherein said control circuit, in response to receiving an electrical signal from said metering device, calculates the rate in which fluid passes through the lumen.

7. The combination as claimed in claim 3 wherein said control circuit has time monitoring capabilities.

8. The combination as claimed in claim 7 wherein said control circuit comprises a microprocessor and a clock.

9. The combination as claimed in claim 3 wherein said device for monitoring the administration of enteral nutritional fluids further comprises an externally-visible display in electrical connection with said control circuit.

10. The combination as claimed in claim 3 wherein said device for monitoring the administration of enteral nutritional fluids further comprises at least one externally accessible user input device in electrical connection with said control circuit.

11. The combination as claimed in claim 3 wherein said device for monitoring the administration of enteral nutritional fluids further comprises an alarm in electrical connection with said control circuit.

12. The combination as claimed in claim 3 wherein said feeding tube is a gastrostomy feeding tube.

13. The combination of:

(a) an enteral feeding tube, said enteral feeding tube including a longitudinally-extending bore and an open proximal end, and (b) a device for monitoring the administration of enteral nutritional fluids into the open proximal end of said enteral feeding tube, said device comprising, (i) a casing coupled to the open proximal end of said enteral feeding tube, said casing being shaped to define a lumen in fluid communication with the longitudinally-extending bore of said enteral feeding tube, said lumen including an inlet and an outlet, wherein said casing includes a lower housing and an upper housing which are pivotally connected together about a hinge, (ii) an electronic control circuit mounted within said casing, and (iii) a metering device in electrical connection with the electronic control circuit, wherein the metering device is positioned within the lumen of the casing to measure fluid flow therethrough.

14. The combination as claimed in claim 13 wherein said upper housing can be pivoted relative to said lower housing between an open position and a closed position.

15. The combination as claimed in claim 14 wherein said casing includes a tube connector which is coupled to the open proximal end of said enteral feeding tube.

16. The combination as claimed in claim 15 wherein said tube connector is shaped to include at least one outwardly projecting barb.

17. The combination of:

(a) a feeding tube, said feeding tube including a longitudinally-extending bore and an open proximal end, and (b) a device for monitoring the administration of enteral nutritional fluids into the open proximal end of said feeding tube, said device comprising, (i) a casing coupled to the open proximal end of said feeding tube, said casing being shaped to define a lumen in fluid communication with the longitudinally-extending bore of said feeding tube, said lumen including an inlet and an outlet, wherein said casing includes a lower housing and an upper housing which are pivotally connected together about a hinge, wherein said upper housing can be pivoted relative to said lower housing between an open position and a closed position, wherein said casing comprises a protrusion which fittingly projects into the inlet of said lumen when said upper housing is disposed in its closed position, and (ii) an electronic control circuit mounted within said casing.

18. The combination as claimed in claim 17 wherein said casing is provided with a locking member for releasably retaining the upper housing in its closed position.

19. The combination of:

(a) an enteral feeding tube, said enteral feeding tube including a longitudinally-extending bore and an open proximal end, and (b) a device for monitoring the administration of enteral nutritional fluids into the open proximal end of said enteral feeding tube, said device comprising, (i) a casing coupled to the open proximal end of said enteral feeding tube, said casing being shaped to define a lumen in fluid communication with the longitudinally-extending bore of said enteral feeding tube, said lumen including an inlet and an outlet, wherein said casing includes a lower housing and an upper housing which are pivotally connected together about a hinge, wherein said upper housing can be pivoted relative to said lower housing between an open position and a closed position, (ii) an electronic control circuit mounted within said casing, and (iii) a pressure sensor in electrical connection with said control circuit.

20. The combination as claimed in claim 19 wherein said pressure sensor is fixedly mounted to said casing.

21. The combination as claimed in claim 20 wherein said pressure sensor generates an electrical signal when said upper housing is disposed in its closed position.

22. A device for monitoring the administration of enteral nutritional fluids into the open proximal end of a feeding tube, said feeding tube including a longitudinally-extending bore and an open proximal end, said device comprising:

(i) a casing shaped to comprise an upper housing and a lower housing, said lower housing being shaped to comprise a top surface, a bottom surface and a lumen, said lumen extending transversely relative to said top and bottom surfaces and including an inlet and an outlet, said inlet being provided in said top surface, said casing being adapted to be coupled to the open proximal end of said feeding tube such that the lumen is in fluid communication with the longitudinally-extending bore, and (ii) an electronic control circuit mounted within said casing.

23. The device for monitoring the administration of enteral nutritional fluids as claimed in claim 22 further comprising a metering device in electrical connection with said control circuit.

24. The device for monitoring the administration of enteral nutritional fluids as claimed in claim 23 wherein said metering device is coupled to said casing.

25. The device for monitoring the administration of enteral nutritional fluids as claimed in claim 22 wherein said control circuit has time monitoring capabilities.

26. The device for monitoring the administration of enteral nutritional fluids as claimed in claim 25 wherein said control circuit comprises a microprocessor and a clock.

27. A device for monitoring the administration of enteral nutritional fluids into the open proximal end of a feeding tube, said feeding tube including a longitudinally-extending bore and an open proximal end, said device comprising:

(i) a casing shaped to define a lumen, said lumen including an inlet and an outlet, said casing being adapted to be coupled to the open proximal end of said feeding tube such that the lumen is in fluid communication with the longitudinally-extending bore, (ii) an electronic control circuit mounted within said casing, (iii) a metering device in electrical connection with said control circuit, wherein said metering device is positioned within the lumen and coupled to said casing.

28. The device for monitoring the administration of enteral nutritional fluids as claimed in claim 27 wherein said metering device includes a pressure-sensitive material which generates an electrical signal in response to fluid passing through the lumen.

29. The device for monitoring the administration of enteral nutritional fluids as claimed in claim 28 wherein said control circuit, in response to receiving an electrical signal from said metering device, calculates the amount of fluid which passes through the lumen.

30. The device for monitoring the administration of enteral nutritional fluids as claimed in claim 28 wherein said control circuit, in response to receiving an electrical signal from said metering device, calculates the rate in which fluid passes through the lumen.

31. A device for monitoring the administration of enteral nutritional fluids into the open proximal end of a feeding tube, said feeding tube including a longitudinally-extending bore and an open proximal end, said device comprising:

(i) a casing comprising a lower housing and an upper housing which are pivotally connected together about a hinge, said lower housing being shaped to include a top surface, a bottom surface, and a tube connector, said tube connector being adapted to be fluidly coupled to the open proximal end of said feeding tube, said tube connector extending transversely through said top surface and said bottom surface of said lower housing; and (ii) an electronic control circuit mounted within said casing.

32. The device for monitoring the administration of enteral nutritional fluids as claimed in claim 31 wherein said upper housing can be pivoted relative to said lower housing between an open position and a closed position.

33. The device for monitoring the administration of enteral nutritional fluids as claimed in claim 32 wherein said casing is provided with a locking member for releasably retaining the upper housing in its closed position.

34. The device for monitoring the administration of enteral nutritional fluids as claimed in claim 32 wherein said device for monitoring the administration of enteral nutritional fluids further comprises a pressure sensor in electrical connection with said control circuit.

35. The device for monitoring the administration of enteral nutritional fluids as claimed in claim 34 wherein said pressure sensor is fixedly mounted to said casing.

36. The device for monitoring the administration of enteral nutritional fluids as claimed in claim 35 wherein said pressure sensor generates an electrical signal when said upper housing is disposed in its closed position.

37. The device for monitoring the administration of enteral nutritional fluids as claimed in claim 31 wherein said tube connector is shaped to include at least one outwardly projecting barb.

38. A device for monitoring the administration of enteral nutritional fluids into the open proximal end of a feeding tube, said feeding tube including a longitudinally-extending bore and an open proximal end, said device comprising:

(i) a casing shaped to define a lumen, said lumen including an inlet and an outlet, said casing being adapted to be coupled to the open proximal end of said feeding tube such that the lumen is in fluid communication with the longitudinally-extending bore, wherein said casing includes a lower housing and an upper housing which are pivotally connected together about a hinge, wherein said upper housing can be pivoted relative to said lower housing between an open position and a closed position, and wherein said casing comprises a protrusion which fittingly projects into the inlet of said lumen when said upper housing is disposed in its closed position; and (ii) an electronic control circuit mounted within said casing.

39. The combination of:

(a) an enteral feeding tube, the enteral feeding tube including a longitudinally-extending bore and an open proximal end, and (b) a device for monitoring the administration of enteral nutritional fluids into the open proximal end of the enteral feeding tube, the device comprising, (i) a casing, the casing including a connector coupled to the open proximal end of the enteral feeding tube, the connector being shaped to define a lumen in fluid communication with the longitudinally-extending bore of the enteral feeding tube, the lumen including an inlet and an outlet, (ii) an electronic control circuit mounted within the casing, and (iii) a metering device in electrical connection with the electronic control circuit, wherein the metering device is positioned within the lumen of the connector to measure fluid flow therethrough.

40. The combination as claimed in claim 39 wherein the connector of the casing is inserted into the enteral feeding tube.

41. A device for monitoring the administration of enteral nutritional fluids into the open proximal end of a feeding tube, said feeding tube including a longitudinally-extending bore and an open proximal end, said device comprising:

(a) a casing, said casing comprising a first portion and a second portion, said first portion and said second portion being pivotally connected about a hinge so that the casing is alternately positionable in an open position and a closed position, said first portion of said casing being shaped to include a tubular connector, said tubular connector having an inlet and an outlet, said outlet being adapted to be coupled to the open proximal end of a feeding tube, said inlet being open to the passage of fluid therethrough when the casing is in said open position and being closed to the passage of fluid therethrough when the casing is in said closed position;

(b) a metering device, said metering device being coupled to said tubular connector to measure fluid flow therethrough; and (c) an electronic control circuit, said electronic control circuit being electrically coupled to said metering device.

* * * * *